United States Patent [19]

Nakai

[11] Patent Number: 5,051,425

[45] Date of Patent: Sep. 24, 1991

[54] THERAPEUTIC COMPOSITION FOR COMBATTING AIDS

[76] Inventor: Masuyo Nakai, 5-8, Hama 2-chome, Amagasaki-shi, Hyogo, Japan

[21] Appl. No.: 215,953

[22] Filed: Jul. 6, 1988

[30] Foreign Application Priority Data

Aug. 3, 1987 [JP] Japan .............................. 62-193991

[51] Int. Cl.$^5$ ................... A61K 31/505; A61K 31/70; A61K 31/66; A61K 31/13
[52] U.S. Cl. ..................................... 514/256; 514/45; 514/49; 514/110; 514/274; 514/644
[58] Field of Search ......................................... 514/256

[56] References Cited

PUBLICATIONS

Chemical Abstracts, 92: 135417m (1980) as define in 10th Collective Index, p. 54712cs (vol. 1).
Chemical Abstracts, 93: 13083z (1980).
Balzarini et al., *Mol. Pharmacol.*, 32:162–167 (1987).
Robins, *Pharmaceutical Res.*, 1:11–17 (1984).
Gill et al., *Proc. Annu. Meet. Am. Soc. Clin. Oncol.*, 5:5 (1986) (Abstract).
Gill et al., Third International Conference on Malignant Lymphoma (Jun. 10–13, 1987) (Abstract).
Gill et al., *Proceedings of Asco*, 5:5 (1986) (Abstract).
Gill et al., *J. Clin. Oncol.*, 5:1322–1328 (1987).
Harada et al., *Virol.*, 146:272–281 (1985).
Sarin et al., *Nato Asi Ser. Ser A*, 120:329–342 (1986).

*Primary Examiner*—Jerome D. Goldberg
*Attorney, Agent, or Firm*—Sughrue, Mion, Zinn, Macpeak & Seas

[57] ABSTRACT

A therapeutic composition for combatting acquired immune deficiency syndrome (AIDS) comprising: (A) a pharmaceutically effective amount of at least one carcinostatic agent selected from alkylating agents and antimetabolites and (B) a pharmaceutically acceptable carrier.

1 Claim, No Drawings

THERAPEUTIC COMPOSITION FOR COMBATTING AIDS

FIELD OF THE INVENTION

The present invention relates to a therapeutic composition for combatting acquired immune deficiency syndrome (AIDS).

BACKGROUND OF THE INVENTION

Although attempts have been made to develop a therapeutic composition for combatting AIDS, no effective composition has at present been found.

SUMMARY OF THE INVENTION

Accordingly, an object of the present invention is to provide an excellent therapeutic composition for combatting AIDS.

The above-described object has been met by a therapeutic composition for combatting AIDS comprising (A) a pharmaceutically effective amount of a carcinostatic agent selected from the group consisting of an alkylating agent and an antimetabolite and (B) a pharmaceutically acceptable carrier.

DETAILED DESCRIPTION OF THE INVENTION

The present invention relates to a therapeutic composition for combatting AIDS comprising: (A) a pharmaceutically effective amount of at least one carcinostatic agent selected from alkylating agents and antimetabolites and (B) a pharmaceutically acceptable carrier.

(1) Carcinostatic agent

Examples of the alkylating agents include nitrogen mustard-N-oxide, cyclophosphamide and nimustine-HCl.

Examples of the antimetabolites include 5-fluorouracil, ancitabine-HCl, thioinosine and cytarabine.

These agents may be used in combination.

The carcinostatic agents used in the present invention are commercially available.

The carcinostatic agents are appropriately mixed with a pharmaceutically acceptable carrier to prepare pharmaceutical compositions.

In the case of oral administration, examples of a pharmaceutically acceptable carrier used include lactose, starch, sucrose, glucose, crystalline cellulose, calcium carbonate, kaolin, stearic acid, magnesium stearate, talc, gelatin, sodium carboxymethyl cellulose, methyl cellulose, silicic acid anhydride.

In the case of injection, the carcinostatic agent is dissolved in a pharmaceutically acceptable solution such as distilled water for injection, physiological saline, an injectable solution containing sugar (e.g., sucrose, fructose, xylitol), Ringer's solution, an electrolytic solution, a sugar-containing electrolytic solution.

(2) Dose

The antiviral activity of each carcinostatic agent can be determined in vitro within the cytotoxic limitation thereof. Thus, the therapeutic composition for combatting AIDS of the present invention can be administered at a dose up to the maximum level, i.e., cytotoxic limit, of each carcinostatic agent.

Specifically, the therapeutic composition of the present invention can be administered at a dosage of, for example, 10–100 mg/day (intravenous injection) in terms of the amount of nitrogen mustard-N-oxide, 100–200 mg/day (oral administration) or 100–500 mg/day (intravenous injection) in terms of the amount of cyclophosphamide, 2–3 mg/kg of body weight/day (intravenous injection) in terms of the amount of nimustine-HCl, 200–300 mg/day (oral administration), 5–20 mg/kg of body weight/day (intravenous injection), or 100–200 mg/day (rectal suppository) in terms of the amount of 5-fluorouracil, 8–20 mg/kg of body weight/day (intravenous injection) in terms of the amount of ancitabine-HCl, 50–300 mg/day (oral administration) or 100–750 mg/day (intravenous injection) in terms of the amount of thioinosine, and 0.2–2 mg/kg of body weight/day (intravenous injection) in terms of the amount of cytarabine.

(3) Mode of administration

The therapeutic composition for combatting AIDS of the present invention may be administered in a conventional manner employed for each carcinostatic agent. For example, each composition containing a carcinostatic agent according to the present invention is administered in the following manner: injection into vein, plural cavity, peritoneal cavity or tumor tissue for the composition containing nitrogen mustard-N-oxide; oral administration, injection into vein, muscular, peritoneal cavity or tumor tissue, or local perfusion for the composition containing cyclophosphamide; intravenous or intraarterial injection for the composition containing nimustine-HCl; oral administration, or intravenous or intrarectal injection for the composition containing 5-fluorouracil; intravenous or intraarterial injection for the composition containing ancitabine-HCl; oral administration or intravenous injection for the composition containing thioinosine; intravenous, intraarterial, subcutaneous or intramuscular injection for the composition containing cytarabine.

The present invention is illustrated in detail with reference to the following non-limiting example.

EXAMPLE

A. Materials and Methods (1) Specimen: Alkylating agents and antimetabolites as shown in the table below.

(2) Virus: HIV-I (HTLV-III strain)

(3) Target cell: MT-4 cells (Jpn. J. Concer. Res., 28, 219–228 (1982))

(4) Evaluation of the effects of the carcinostatic agent (i) Pretreatment

Fifty $\mu$l/well portions of the target cells ($5 \times 10^6$ cells/ml) were pipetted into two-fold serial dilution samples of each carcinostatic agent (50 $\mu$l/well). These mixture were allowed to react at 37° C. under $CO_2$ atmosphere for 18 to 24 hours and then inoculated with 100 $\mu$l/well (50–500 $TCID_{50}$) of a HIV-I viral solution.

(ii) Simultaneous treatment

Fifty $\mu$l/well portions of the target cells ($5 \times 10^6$ cells/ml) were pipetted into two-fold serial dilution samples of each carcinostatic agent (50 $\mu$l/well) and then inoculated with 100 $\mu$l/well (50–500 $TCID_{50}$) of a HIV-I viral solution.

(iii) The mixtures obtained in (i) and (ii) above were incubated at 37° C. for three days. Then the culture medium was replaced and incubation was further continued for three to four days. The anti HIV-I virus activity of each sample was evaluated based on the anticytopathogenic activity thereof.

B. Result

The table below shows the growth-inhibition concentration of each carcinostatic agent on the HIV-I strain.

In the table below, the expression "pretreatment" means the case where the target cells were treated with a carcinostatic agent before inoculation with the HIV-I strain, while the expression "simultaneous treatment" means the case where the treatment with the carcinostatic agent was effected simultaneously with inoculation of the virus. The "cytotoxic effect" means the dose at which each carcinostatic agent showed a cytotoxic effect.

TABLE

| Compound | Pretreatment ($\mu$g/ml) | Simultaneous treatment ($\mu$g/ml) | Cytotoxic effect ($\mu$g/ml) |
| --- | --- | --- | --- |
| Nitrogen mustard-N-oxide HCl[1] | 2-15 | 5-30 | 50-100 |
| Cyclophosphamide[2] | 1-10 | 5-30 | 100-500 |
| Nimustine-HCl[3] | 1-10 | 5-30 | 100-500 |
| 5-Fluorouracil[4] | <1 | <1 | 50-150 |
| Ancitabine-HCl[5] | <1 | <1 | 50-150 |
| Thioinosine[6] | <1 | <1 | 10-100 |
| Cytarabine[7] | <1 | <1 | 5-50 |

Note:
Commercial source of each carcinostatic agent is listed below.
[1]Yoshitomi Pharmaceutical
[2]Yamanouchi Pharmaceutical
[3]Sankyo
[4]Kyowa Hakko Kogyo
[5]Kohjin-Yamanouchi Pharmaceutical
[6]Morishita Pharmaceutical
[7]Sumitomo Chemical-Upjohn Japan From the results shown in the table above, it can be seen that, among carcinostatic agents, alkylating agents and antimetabolites exert anti-HIV-I activity and thus are effective in a therapeutic composition for combatting AIDS.

While the invention has been described in detail and with reference to specific embodiments thereof, it will be apparent to one skilled in the art that various changes and modifications can be made therein without departing from the spirit and scope thereof.

What is claimed is:

1. A method of treating AIDS which comprises administering to a subject afflicted with AIDS an anti-AIDS pharmaceutically effective amount of an alkylating agent, wherein said alkylating agent is nimustine-HCl, and a pharmaceutically acceptable carrier.

* * * * *